United States Patent
Kimoto

(10) Patent No.: US 9,530,203 B2
(45) Date of Patent: Dec. 27, 2016

(54) IMAGE PROCESSING APPARATUS AND IMAGE PROCESSING METHOD

(71) Applicant: Toshiba Medical Systems Corporation, Otawara-shi (JP)

(72) Inventor: Tatsuya Kimoto, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 1 day.

(21) Appl. No.: 13/851,396

(22) Filed: Mar. 27, 2013

(65) Prior Publication Data

US 2013/0223687 A1 Aug. 29, 2013

Related U.S. Application Data

(63) Continuation of application No. PCT/JP2011/073319, filed on Oct. 11, 2011.

(30) Foreign Application Priority Data

Oct. 11, 2011 (JP) ................. 2010-228766

(51) Int. Cl.
*G06K 9/00* (2006.01)
*G06T 7/00* (2006.01)
(Continued)

(52) U.S. Cl.
CPC ............. *G06T 7/0012* (2013.01); *A61B 6/032* (2013.01); *A61B 6/50* (2013.01); *A61B 6/5217* (2013.01);
(Continued)

(58) Field of Classification Search
CPC ................. G06T 7/0012; G06T 2207/10081; G06T 2207/30061; G06T 7/0081; G06T 2207/30004
See application file for complete search history.

(56) References Cited

U.S. PATENT DOCUMENTS

2002/0009215 A1 1/2002 Armato, III et al.
2003/0099386 A1* 5/2003 Schneider et al. ............ 382/130
(Continued)

FOREIGN PATENT DOCUMENTS

CN 1418353 A 5/2003
JP 7-28976 1/1995
(Continued)

OTHER PUBLICATIONS

International Search Report issued on Nov. 15, 2011 for PCT/JP2011/073319 filed on Oct. 11, 2011 with English Translation.
(Continued)

*Primary Examiner* — Stephen R Koziol
*Assistant Examiner* — Jonathan S Lee
(74) *Attorney, Agent, or Firm* — Oblon, McClelland, Maier & Neustadt, L.L.P.

(57) ABSTRACT

An image processing apparatus according to an embodiment includes a lung field region extracting unit, a lung field bottom region extracting unit, and a detecting unit. The lung field region extracting unit is configured to extract, based on pixel values of pixels constituting a three-dimensional medical image capturing a chest of a subject, a lung field region from the three-dimensional medical image. The lung field bottom region extracting unit is configured to extract a lung field bottom region from the lung field region. The detecting unit is configured to detect a vertex position of the lung field bottom region on the head side of the subject.

5 Claims, 7 Drawing Sheets

(51) Int. Cl.
*A61B 6/03* (2006.01)
*A61B 5/055* (2006.01)
*A61B 6/00* (2006.01)

(52) U.S. Cl.
CPC ........... *G06T 7/0081* (2013.01); *G06T 7/0091* (2013.01); *A61B 5/055* (2013.01); *A61B 6/4085* (2013.01); *A61B 6/463* (2013.01); *A61B 6/5223* (2013.01); *G06T 2207/10072* (2013.01); *G06T 2207/20101* (2013.01); *G06T 2207/20148* (2013.01); *G06T 2207/30061* (2013.01)

(56) References Cited

U.S. PATENT DOCUMENTS

| | | | |
|---|---|---|---|
| 2003/0099390 A1* | 5/2003 | Zeng et al. | 382/131 |
| 2004/0101180 A1* | 5/2004 | Doi | G06T 7/0012 |
| | | | 382/128 |
| 2005/0063579 A1* | 3/2005 | Lee | G06K 9/34 |
| | | | 382/131 |
| 2006/0004282 A1* | 1/2006 | Oosawa | G06K 9/4609 |
| | | | 600/416 |
| 2009/0052754 A1* | 2/2009 | Goto et al. | 382/128 |
| 2009/0087072 A1* | 4/2009 | Hong | G06T 7/0083 |
| | | | 382/132 |
| 2013/0156267 A1* | 6/2013 | Muraoka | A61B 6/507 |
| | | | 382/103 |

FOREIGN PATENT DOCUMENTS

| | | |
|---|---|---|
| JP | 2002-503861 A | 2/2002 |
| JP | 2003-523801 | 8/2003 |
| JP | 2007-185250 | 7/2007 |
| JP | 2007-300966 | 11/2007 |
| WO | 2006/137294 | 12/2006 |
| WO | 2007/094412 | 8/2007 |

OTHER PUBLICATIONS

International Written Opinion issued on Nov. 15, 2011 for PCT/JP2011/073319 filed on Oct. 11, 2011.

Combined Office Action and Search Report issued Dec. 10, 2013 in Chinese Patent Application No. 201180002837.4 (with English translation of category of cited documents).

Japanese Office Action issued Oct. 13, 2015 in corresponding Japanese Patent Application No. 2011-223217 (2 pages).

\* cited by examiner

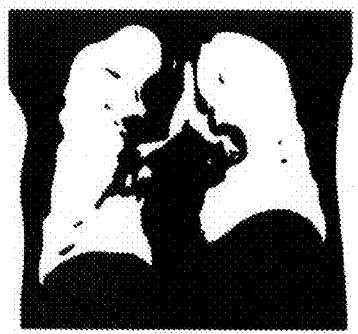
FIG.3A
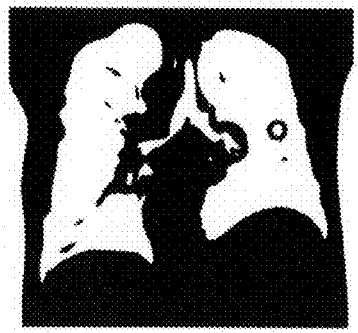
FIG.3B
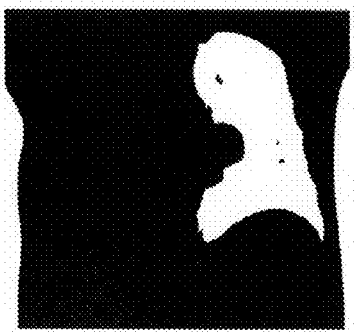

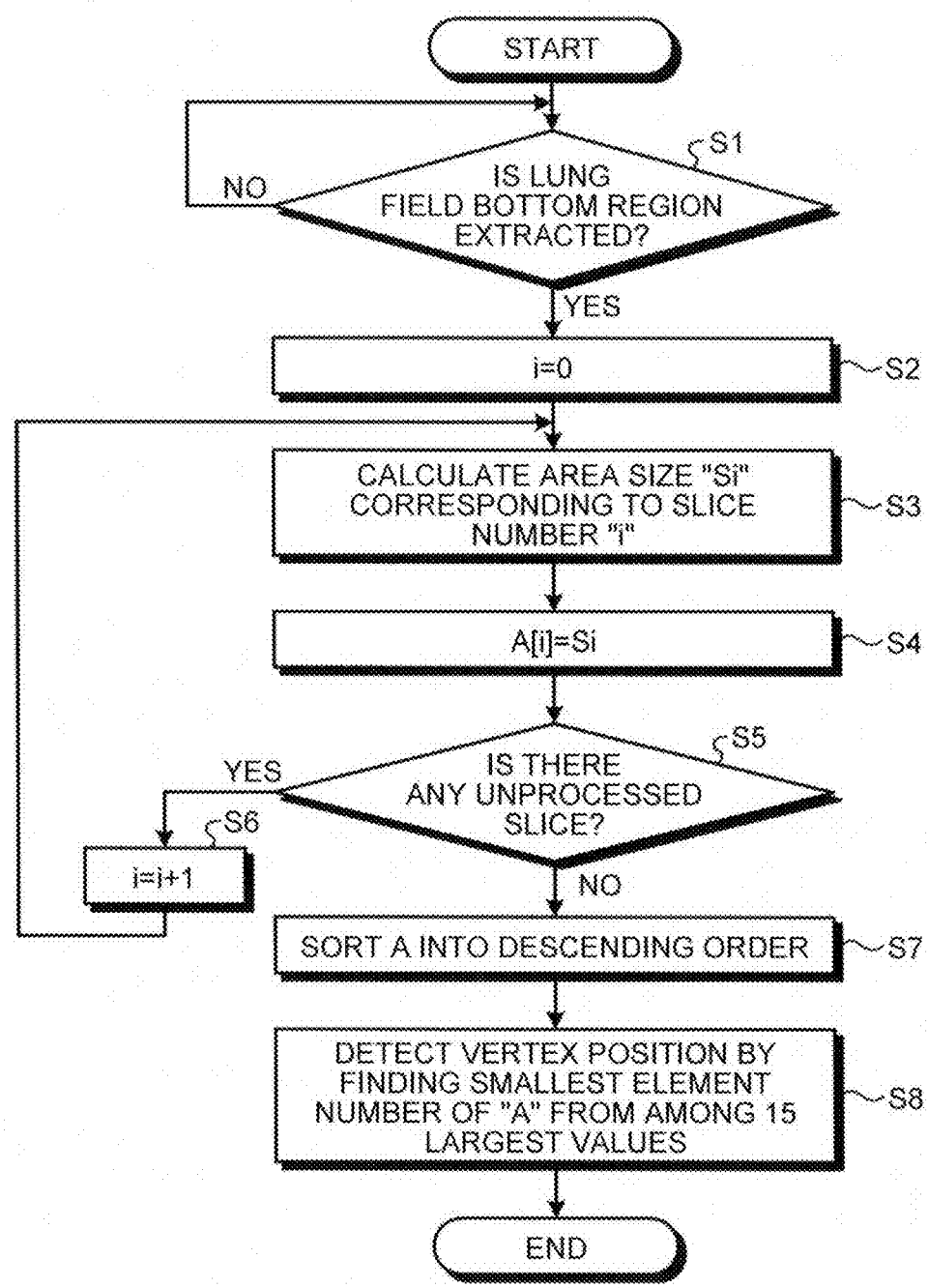

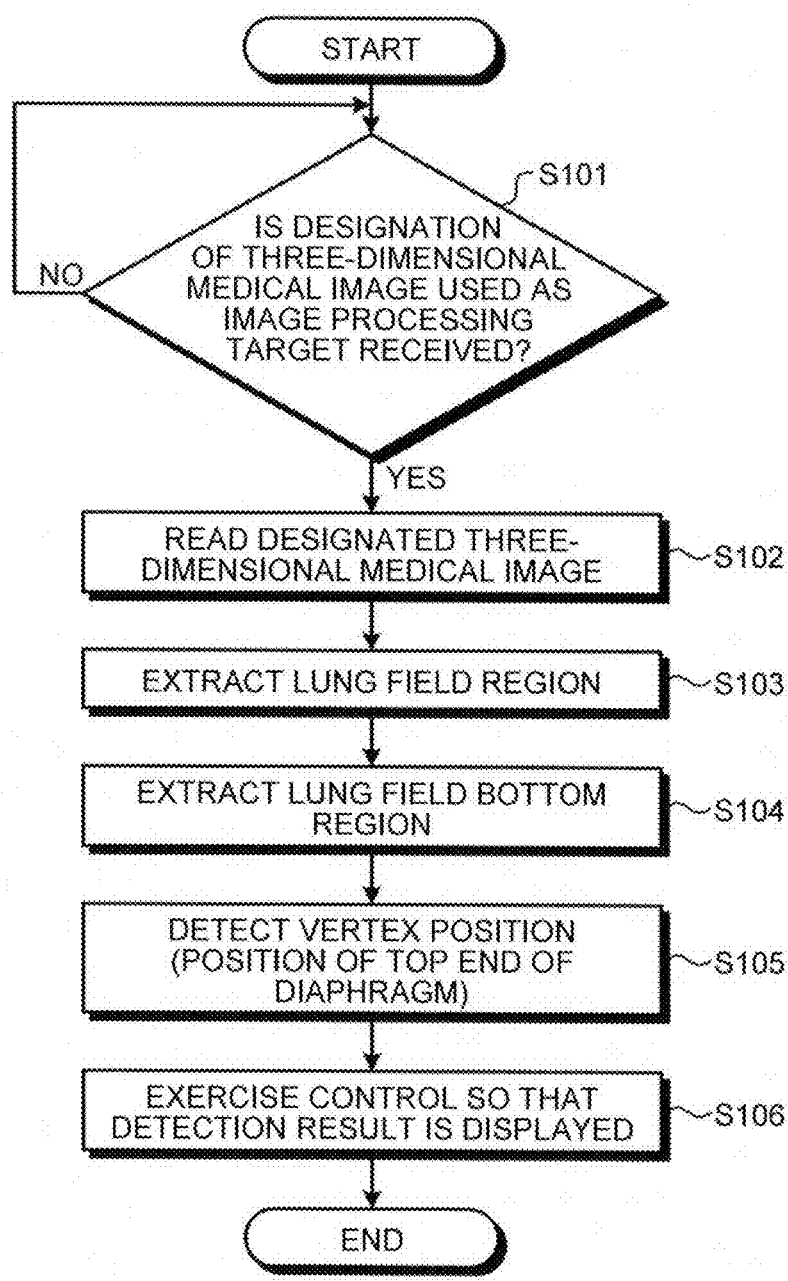

IMAGE PROCESSING APPARATUS AND IMAGE PROCESSING METHOD

CROSS-REFERENCE TO RELATED APPLICATIONS

This application is a continuation of PCT international application Ser. No. PCT/JP2011/073319 filed on Oct. 11, 2011 which designates the United States, and which claims the benefit of priority from Japanese Patent Application No. 2010-228766, filed on Oct. 8, 2010; the entire contents of which are incorporated herein by reference.

FIELD

Embodiments described herein relate generally to an image processing apparatus and an image processing method.

BACKGROUND

Conventionally, in a guideline for making an image diagnosis of emphysema, a cross-sectional image at an axial plane that goes through the top end of the diaphragm is specified as one of medical images that should be referred to by a medical doctor.

For an image diagnosis of emphysema, first, a three-dimensional medical image of a chest of a subject is taken by using a medical image diagnosis apparatus such as an X-ray Computed Tomography (CT) apparatus, an X-ray diagnosis apparatus, a Magnetic Resonance Imaging (MRI) apparatus, or the like. Further, the medical doctor determines the position of the top end of the diaphragm by visually checking cross-sectional images of the three-dimensional medical image at a coronal plane and at an axial plane. After that, the medical doctor makes an image diagnosis by referring to an axial cross-sectional image at the top end position of the diaphragm and a coronal cross-sectional image in which the top end position of the diaphragm is displayed. More specifically, the medical doctor makes an image diagnosis of emphysema by referring to the size of an emphysema region identified in the cross-sectional images.

It is also known that emphysema makes the position of the diaphragm lower and that interstitial pneumonia makes the position of the diaphragm higher. For this reason also, the position of the top end of the diaphragm is important when making image diagnoses of respiratory system diseases. The position of the diaphragm is also used for judging movements of an image-taking target site caused by breathing or the like during an MRI image taking process.

To visually determine the position of the top end of the diaphragm, however, the viewer needs to observe a plurality of cross-sectional images. Thus, a lot of labor is required, and the efficiency of the process of making an image diagnosis is therefore low. In addition, in some situations, the top end position of the diaphragm that is visually determined does not have reproducibility. In other words, the top end position of the diaphragm that is visually determined is based on a subjective judgment of the viewer. For this reason, the top end position of the diaphragm may vary among different viewers. In addition, the top end position of the diaphragm may vary among determining processes that are performed by a single viewer.

BRIEF DESCRIPTION OF THE DRAWINGS

FIG. 3A and FIG. 3B are drawings for explaining the lung field region extracting unit.

FIG. 5 is a flowchart for explaining a process performed by a detecting unit.

FIG. 8 is a flowchart for explaining a process performed by the image processing apparatus according to the embodiment.

DETAILED DESCRIPTION

An image processing apparatus according to an embodiment includes a lung field region extracting unit, a lung field bottom region extracting unit, and a detecting unit. The lung field region extracting unit is configured to extract, based on pixel values of pixels constituting a three-dimensional medical image capturing a chest of a subject, a lung field region from the three-dimensional medical image. The lung field bottom region extracting unit is configured to extract a lung field bottom region from the lung field region. The detecting unit is configured to detect a vertex position of the lung field bottom region on the head side of the subject.

Embodiments of an image processing apparatus will be explained in detail, with reference to the accompanying drawings. The image processing apparatus according to an embodiment is an apparatus configured to detect the position of a top end of the diaphragm by using a three-dimensional medical image of a chest of a subject taken by a medical image diagnosis apparatus such as an X-ray Computed Tomography (CT) apparatus, an X-ray diagnosis apparatus, an Magnetic Resonance Imaging (MRI) apparatus, or the like.

Figure 1:
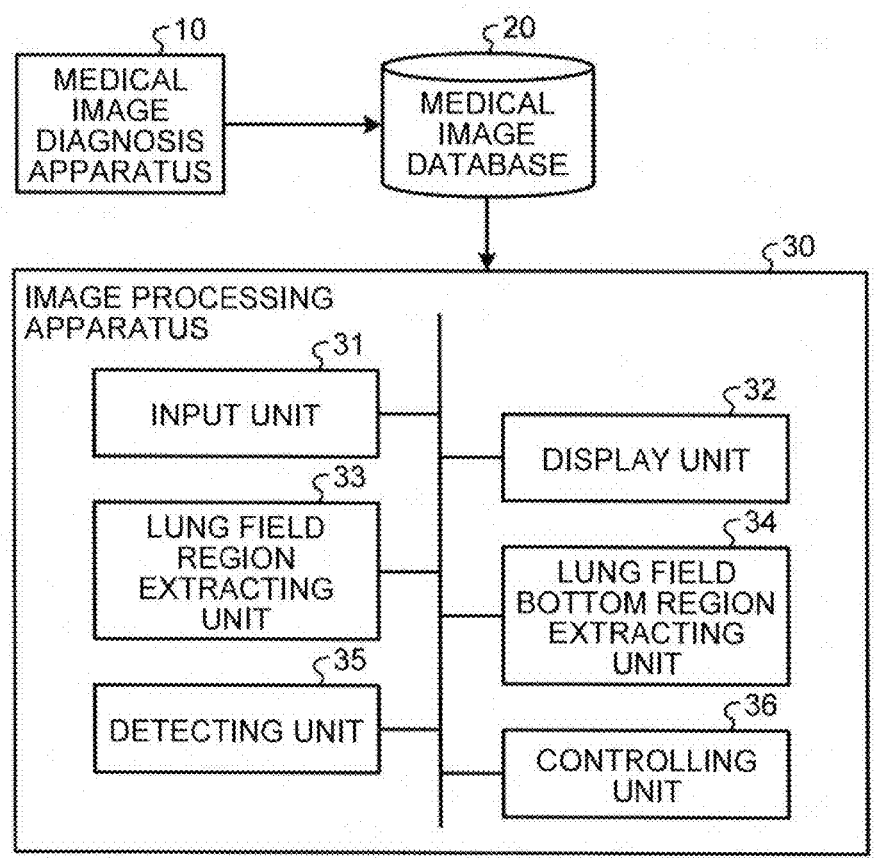
FIG. 1 is a drawing for explaining a configuration of an image processing apparatus according to an embodiment.

First, a configuration of the image processing apparatus according to the present embodiment will be explained, with reference to FIG. 1. FIG. 1 is a drawing for explaining a configuration of the image processing apparatus according to the present embodiment.

As shown in FIG. 1, an image processing apparatus 30 according to the present embodiment is connected to a medical image database 20. Further, the medical image database 20 is connected to a medical image diagnosis apparatus 10.

Figure 2:
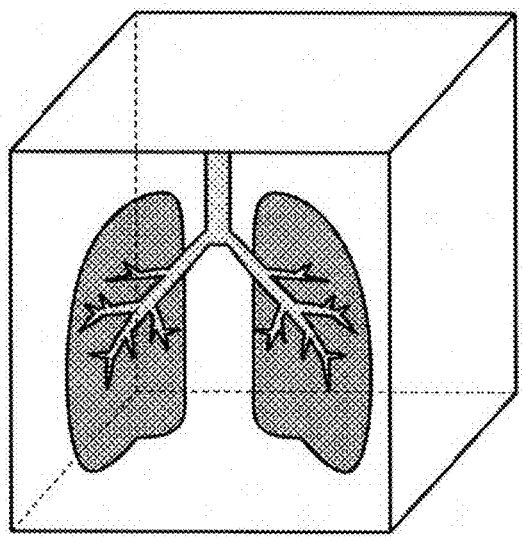
FIG. 2 is a drawing for explaining an example of data used as a target of an image processing process performed by the image processing apparatus according to the embodiment.

The medical image diagnosis apparatus 10 is a medical image diagnosis apparatus such as an X-ray CT apparatus, an X-ray diagnosis apparatus, an MRI apparatus, or the like. The medical image database 20 is, for example, a database for a Picture Archiving and Communication System (PACS), which is a system configured to manage data of various types of medical images, or a database for an electronic health record system configured to manage electronic health records to which medical images are attached. More specifically, the medical image database 20 stores therein one or more three-dimensional medical images capturing the chest of the subject who underwent a medical examination for emphysema. FIG. 2 is a drawing for explaining an example of data used as a target (hereinafter, "image processing target") of an image processing process performed by the image processing apparatus according to the present embodiment.

For example, as shown in FIG. 2, the medical image database 20 stores therein a three-dimensional X-ray CT image used as an image processing target of the image processing apparatus 30, i.e., a three-dimensional X-ray CT image obtained by taking an image of the chest of the subject who underwent the medical examination for emphysema, by using an X-ray CT apparatus serving as the medical image diagnosis apparatus 10.

In the following sections, an example will be explained in which the three-dimensional X-ray CT image capturing the chest of the subject is the image processing target of the image processing apparatus 30. However, the present embodiment is also applicable to a situation where the image processing target of the image processing apparatus 30 is a three-dimensional MRI image capturing the chest of the subject or a three-dimensional X-ray image capturing the chest of the subject.

Returning to the description of FIG. 1, the image processing apparatus 30 according to the present embodiment includes an input unit 31, a display unit 32, a lung field region extracting unit 33, a lung field bottom region extracting unit 34, a detecting unit 35, and a controlling unit 36.

The input unit 31 includes a mouse, a keyboard, and the like and receives various types of setting requests from an operator of the image processing apparatus 30. For example, the input unit 31 receives a designation of a three-dimensional X-ray CT image to be used as the image processing target, from the operator. Accordingly, the image processing apparatus 30 obtains the three-dimensional X-ray CT image designated by the operator from the medical image database 20, through a process performed by the controlling unit 36, which is explained later.

The display unit 32 includes a monitor such as a liquid crystal display device or a Cathode-Ray Tube (CRT) display device, or the like. The display unit 32 displays a Graphical User Interface (GUI) used for receiving a command from the operator via the input unit 31, and also, displays a result of the image processing process performed by the image processing apparatus 30.

The lung field region extracting unit 33 extracts a lung field region from the three-dimensional medical image, based on pixel values of pixels constituting the three-dimensional medical image used as the image processing target. More specifically, first, the lung field region extracting unit 33 extracts an air region by identifying pixels of each of which the pixel value is equal to or smaller than a predetermined threshold value from among the pixels constituting the three-dimensional medical image. FIGS. 3A and 3B are drawings for explaining the lung field region extracting unit.

For example, the lung field region extracting unit 33 extracts the air region, as shown in FIG. 3A, by identifying a low CT value region in which the CT values are each equal to or smaller than a "threshold value: −950 HU", which is considered to be the CT value of the air, from among the pixels constituting the three-dimensional X-ray CT image. In the example shown in FIG. 3, the lung field region extracting unit 33 generates a binarized image in which the air region is rendered white, by performing a binarization process to arrange the pixel values in the region equal to or smaller than the threshold value to be "1" and to arrange the pixel values in the region larger than the threshold value to be "0". Although the binarized image of the air region is shown in two dimensions in FIG. 3A, the binarized image of the air region generated by the lung field region extracting unit 33 is a three-dimensional image in actuality.

Further, by implementing a region growing method while using one of the pixels in the air region as a seed point, the lung field region extracting unit 33 extracts a lung field region. Although the diaphragm is in contact with a bottom part of the lung field, because anatomically the liver is positioned on the right-hand side, the position of a top end of the diaphragm in the right lung field is higher than the position of a top end of the diaphragm in the left lung field. For this reason, in the present embodiment, the lung field region extracting unit 33 extracts the right lung field region by implementing the region growing method while using one of the pixels in a region positioned on the right-hand side of the subject within the air region, as a seed point.

For example, as shown on the left-hand side of FIG. 3B, the lung field region extracting unit 33 uses one of the pixels in a right-side region of the air region as a seed point. Further, the lung field region extracting unit 33 grows the region in which the pixel values are "1" by sequentially identifying the pixels of which the pixel value is "1" while using the seed point as a starting point. As a result, the lung field region extracting unit 33 extracts a right lung field region, as shown on the right-hand side of FIG. 3B. In the example shown in FIG. 3B, the lung field region extracting unit 33 generates a binarized image in which the right lung field region is rendered white, by performing a binarization process to arrange the pixel values in the region extracted as the right lung field region by the region growing method to be "1" and to arrange the pixel values in the region other than the right lung field region to be "0". Although the binarized image of the right lung field region is shown in two dimensions on the right-hand side of FIG. 3B, the binarized image of the right lung field region generated by the lung field region extracting unit 33 is a three-dimensional image in actuality.

In this situation, the seed point may be set by the operator or may be set by the lung field region extracting unit 33. When the operator manually sets the seed point, for example, based on an instruction input by the operator via the input unit 31, the controlling unit 36 (explained later) generates a coronal cross-sectional image from the three-dimensional binarized image of the air region shown in FIG. 3A and causes the display unit 32 to display the generated coronal cross-sectional image. After that, the operator sets the pixel used as the seed point via the input unit 31, by referring to the displayed coronal cross-sectional image.

In contrast, when the seed point is set automatically, the lung field region extracting unit 33 detects, from the air region, a pixel having a high possibility of being in the right lung field region. More specifically, the lung field region extracting unit 33 divides image data (the three-dimensional binarized image of the air region) into a left portion and a right portion each having half the size of the image. For example, the lung field region extracting unit 33 divides the image data into a right half and a left half of the subject by referring to additional information appended to the image data such as the posture of the subject during the image taking process and information regarding a coordinate system of the medical image diagnosis apparatus 10. Further, the lung field region extracting unit 33 detects, for example, a pixel positioned at the center of the image data of the right half as the pixel having a high possibility of being in the right lung field region and sets the detected pixel as the seed point.

Alternatively, when the seed point is set automatically, for example, the lung field region extracting unit 33 extracts, from the image data of the right half, a region in which all of the pixel values of the pixels (voxels) are "1" out of a three-dimensional region of a predetermined size, further detects a pixel positioned at the center of the extracted region as the pixel having a high possibility of being in the right lung field region, and sets the detected pixel as the seed point.

Figure 4:
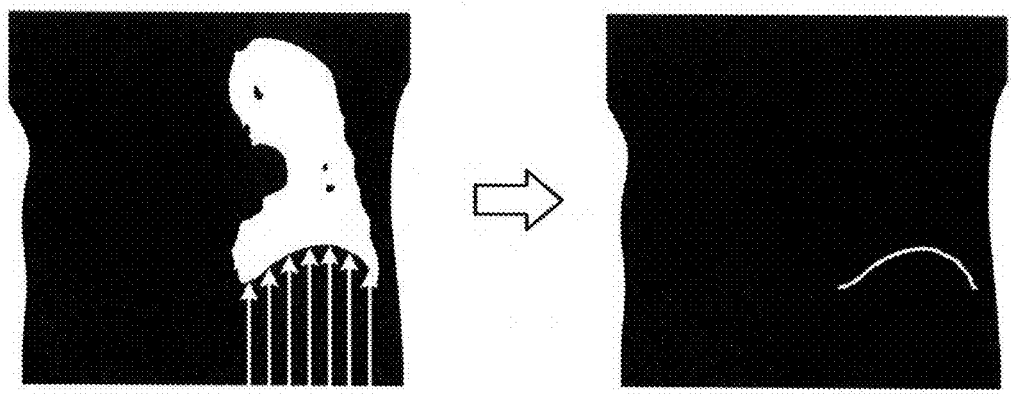
FIG. 4 is a drawing for explaining a lung field bottom region extracting unit.

Returning to the description of FIG. 1, the lung field bottom region extracting unit 34 extracts a lung field bottom region from the lung field region extracted by the lung field region extracting unit 33. More specifically, the lung field bottom region extracting unit 34 judges whether each of the pixels in the three-dimensional medical image is one of the pixels extracted as those in the lung field region, by using a plurality of scanning directions along a body-axis direction extending from the legs toward the head of the subject. Further, the lung field bottom region extracting unit 34 extracts a region formed by the pixels each of which is the first pixel judged to be in the lung field region in a different one of the scanning directions, as the lung field bottom region. In the present embodiment, the lung field bottom region extracting unit 34 extracts the lung field bottom region from the right lung field region extracted by the lung field region extracting unit 33. FIG. 4 is a drawing for explaining the lung field bottom region extracting unit.

More specifically, in the binarized image of the right lung field region, the lung field bottom region extracting unit 34 sets, as shown on the left-hand side of FIG. 4, the plurality of scanning directions along the body-axis direction extending from the legs toward the head of the subject. Further, the lung field bottom region extracting unit 34 judges whether the pixel value of each of the pixels in the scanning direction is "0" or "1". Further, as shown on the right-hand side of FIG. 4, the lung field bottom region extracting unit 34 extracts the region formed by the pixels (the voxels) each of which is the first pixel judged to have a pixel value "1" in a different one of the scanning directions, as the lung field bottom region. In the example shown on the right-hand side of FIG. 4, the lung field bottom region extracting unit 34 generates a binarized image in which the lung field bottom region is rendered white, by performing a binarization process to arrange the pixel values in the region extracted as the lung field bottom region to be "1" and to arrange the pixel values in the region other than the lung field bottom region to be "0". Although the binarized image of the lung field bottom region is shown in two dimensions on the right-hand side of FIG. 4, the binarized image of the lung field bottom region generated by the lung field bottom region extracting unit 34 is a three-dimensional image in actuality. Hereinafter, the lung field bottom region extracted by the lung field bottom region extracting unit 34 may be referred to as a "lung field bottom region mask".

Returning to the description of FIG. 1, the detecting unit 35 detects a vertex position on the head side of the subject from the lung field bottom region extracted by the lung field bottom region extracting unit 34. More specifically, the detecting unit 35 detects the vertex position, based on the area size of the lung field bottom region on each of a plurality of axial planes of the three-dimensional medical image within a range in which the lung field bottom region is present.

In other words, the detecting unit 35 identifies a region that is truly in contact with the diaphragm over a large area in the region extracted as the lung field bottom region and detects the highest position (i.e., the position of the axial plane positioned closest to the head) in the specified region as a top end position of the diaphragm. In the following sections, a specific example of a process performed by the detecting unit 35 will be explained, with reference to FIGS. 5, 6A, 6B, 6C, and 6D. FIG. 5 is a flowchart for explaining the process performed by the detecting unit 35. FIGS. 6A, 6B, 6C, and 6D are drawings for explaining the detecting unit.

First, as shown in FIG. 5, the detecting unit 35 judges whether a lung field bottom region is extracted (step S1). In this situation, if a lung field bottom region is not extracted (step S1: No), the detecting unit 35 goes into a stand-by state.

On the contrary, if a lung field bottom region is extracted (step S1: Yes), the detecting unit 35 sets a slice number "i" to "0" (step S2). In this situation, the slice number "i" is one of the integers in a range that is determined by the quantity of axial cross-sectional images (i.e., the quantity of slices) in which the lung field bottom region mask is present, from among the plurality of axial cross-sectional images constituting the three-dimensional X-ray CT image. For example, if the quantity of slices is "100", the slice number "i" is one of the integers from "0" to "99".

Further, the detecting unit 35 calculates an area size "Si" corresponding to the slice number "i" (step S3), and stores the calculated value "Si" as an array "A[i]" (step S4). Further, the detecting unit 35 judges whether there is any unprocessed slice (step S5). For example, the detecting unit 35 judges whether "i" is "99".

If there are one or more unprocessed slices, i.e., if "i" is an integer smaller than "99" (step S5: Yes), the detecting unit 35 increments "i" so that "i=i+1" is satisfied (step S6), and performs the area size calculating process at step S5.

Figures 6A, 6B, 6C, 6D:
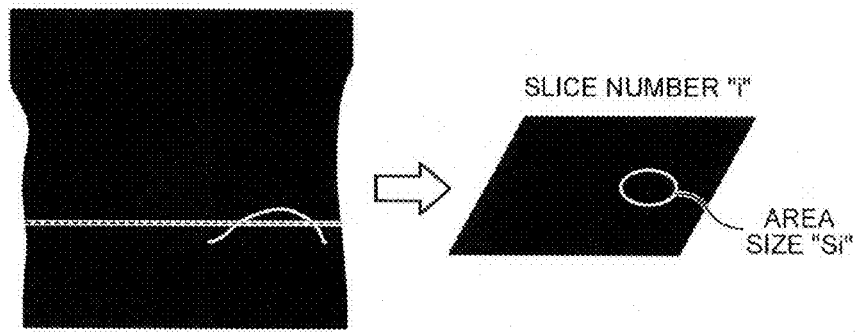
FIG. 6A, FIG. 6B, FIG. 6C, and FIG. 6D are drawings for explaining the detecting unit.

In other words, at step S3, from the binarized image of the lung field bottom region, the detecting unit 35 first generates an axial cross-sectional image corresponding to the slice number "i" that goes through the lung field bottom region mask, as shown in FIG. 6A. Further, at step S3, within the axial cross-sectional image corresponding to the slice number "i", the detecting unit 35 calculates the area size "Si", by counting the quantity of pixels of which the pixel value is "1" and that correspond to the lung field bottom region, as shown in FIG. 6A. After that, at step S4, the detecting unit 35 stores the value "Si" as the array "A[i]".

As a result, as shown in FIG. 6B, the detecting unit 35 stores 100 arrays "A" corresponding to the slice numbers (element numbers) "0" to "99". In other words, as shown in FIG. 6B, the detecting unit 35 stores an array "A[0]=120" indicating the area size corresponding to the slice number "0", an array "A[1]=250" indicating the area size corresponding to the slice number "1", an array "A[50]=185" indicating the area size corresponding to the slice number "50", and so on.

Returning to the description of the flowchart in FIG. 5, if there is no unprocessed slice (step S5: No), the detecting unit 35 sorts the "A" into a descending order based on the area size values (i.e., the quantities of pixels) (step S7). Further, based on the sorted result, the detecting unit 35 detects a vertex position by finding the smallest element number of A, from among the fifteen largest values (step S8), and thus ends the detecting process.

In other words, at step S7, the detecting unit 35 sorts the "A" into the descending order based on the area size values (i.e., the quantities of pixels), as shown in FIG. 6C. After that, at step S7, the detecting unit 35 identifies the arrays having the fifteen largest values, as shown in FIG. 6C. Further, at step S8, the detecting unit 35 detects "i=1" of which the element number (the slice number) is the smallest among the fifteen largest values, as the slice plane (the axial plane) on which the diaphragm top portion is positioned, as shown in FIG. 6D. In the description above, the example is explained in which the quantity of slices is determined according to the quantity of axial cross-sectional images that are reconstructed when the three-dimensional X-ray image is taken; however, the present embodiment is also applicable to another example in which axial cross-sectional images are generated from the binarized image of the right lung field region by using slice intervals that are shorter than those used when the three-dimensional X-ray image is taken, so that the vertex position detecting process is performed with the lung field bottom region mask as described above.

Returning to the description of FIG. 1, the controlling unit 36 exercises overall control of the image processing apparatus 30. In other words, the controlling unit 36 transmits a transfer request for the image data designated by the operator to the medical image database 20 and transfers the image data transferred from the medical image database 20 to the lung field region extracting unit 33. Further, the controlling unit 36 exercises control so that a processing result obtained by the detecting unit 35 is displayed on the display unit 32.

Figure 7A:
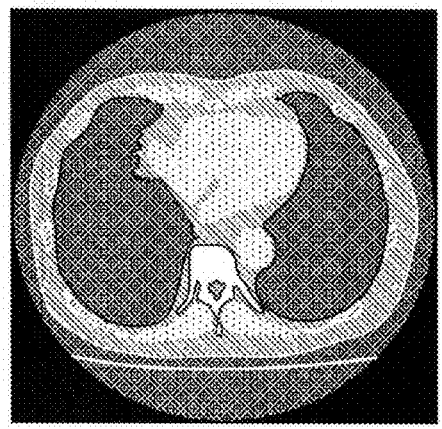
FIG. 7A, FIG. 7B, and FIG. 7C are drawings for explaining yet another exemplary image displayed under the control of the controlling unit.
Figure 7B:
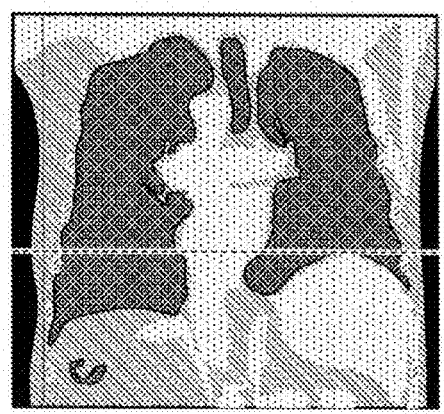
Figure 7C:
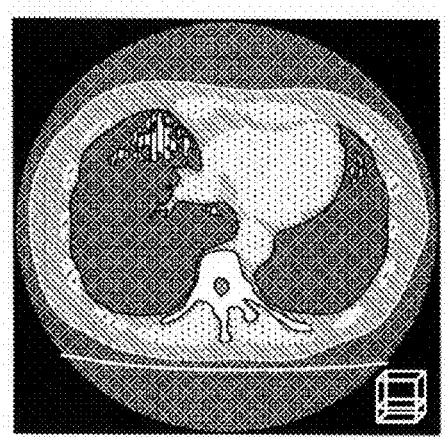

As a specific example, the controlling unit 36 exercises control so that at least one of the following is displayed on the display unit 32: an axial cross-sectional image obtained by sectioning the three-dimensional medical image at the axial plane that goes through the vertex position detected by the detecting unit 35; and a superimposed image obtained by superimposing the position of such an axial cross-sectional image onto another image of the three-dimensional medical image. FIGS. 7A, 7B, and 7C are drawings for explaining examples of images displayed under the control of the controlling unit.

For example, as shown in FIG. 7A, the controlling unit 36 causes the display of an axial cross-sectional image that is obtained by sectioning the three-dimensional X-ray CT image at the axial plane corresponding to the slice number found by the detecting unit 35.

In another example, the controlling unit 36 generates a coronal cross-sectional image from the three-dimensional X-ray CT image. Further, as shown in FIG. 7B, for example, the controlling unit 36 exercises control so that the display unit 32 displays the coronal cross-sectional image while a dotted line indicating the position of the axial plane corresponding to the position of the top portion of the diaphragm is superimposed thereon. In the example shown in FIG. 7B, it is indicated that the top portion of the diaphragm is positioned at the vertex of the right lung field bottom region rendered in the coronal cross-sectional image. Alternatively, it is acceptable for the controlling unit 36 to generate a sagittal cross-sectional image from the three-dimensional X-ray CT image and to exercise control so that the display unit 32 displays the sagittal cross-sectional image while a dotted line indicating the position of the axial plane corresponding to the position of the top portion of the diaphragm is superimposed thereon.

In yet another example, as shown in FIG. 7C, it is acceptable for the controlling unit 36 to extract an emphysema region from an axial cross-sectional image and to further cause the extracted emphysema region to be displayed. Further, it is also acceptable to perform the process of extracting and displaying the emphysema region in the coronal cross-sectional image or in the sagittal cross-sectional image described above. The image on which the position of the axial cross-sectional image is interposed is not limited to the coronal cross-sectional image or the sagittal cross-sectional image of the three-dimensional medical image as described above. The image on which the position of the axial cross-sectional image is interposed may be any other image of the three-dimensional medical image, e.g., a volume rendering image of the three-dimensional medical image, or a Multi Planar Reconstruction (MPR) image obtained by sectioning the three-dimensional medical image at any arbitrary cross section other than a sagittal plane or a coronal plane, or a Maximum Intensity Projection (MIP) image of the three-dimensional medical image.

In the guideline for making an image diagnosis of emphysema, examples of cross sections that should be referred to by medical doctors include axial planes of the upper lung field near the upper edge of the aortic arch, the middle lung field near the tracheal bifurcation, and the lower lung field positioned 1 centimeters to 3 centimeters above the right diaphragm, in addition to an axial plane that goes through the position of the top end of the diaphragm. Accordingly, in addition to the axial plane on which the top portion of the diaphragm is positioned, it is acceptable for the controlling unit 36 to cause such an axial plane to be displayed on which the upper lung field, the middle lung field, or the lower lung field is positioned. Also, it is acceptable for the controlling unit 36 to exercise control so that, in addition to the dotted line indicating the axial plane on which the top portion of the diaphragm is positioned, a dotted line indicating an axial plane on which the upper lung field, the middle lung field, or the lower lung field is positioned is displayed while being superimposed on, for example, a coronal cross-sectional image or a sagittal cross-sectional image. In such a situation, the controlling unit 36 exercises control so that at least one of the following is displayed on the display unit 32: an axial cross-sectional image obtained by sectioning the three-dimensional medical image at an axial plane positioned at a predetermined distance from the vertex position detected by the detecting unit 35; and a superimposed image obtained by superimposing the position of such an axial cross-sectional image onto another image of the three-dimensional medical image. For example, the controlling unit 36 causes the display of an axial cross-sectional image that is obtained by sectioning the three-dimensional medical image at an axial plane positioned 2 centimeters from the vertex position toward the head side. Alternatively, the controlling unit 36 causes the display of a superimposed image that is obtained by, for example, superimposing a dotted line indicating the position of an axial plane positioned 2 centimeters from the vertex position toward the head side, onto another image of the three-dimensional medical image other than the axial cross-sectional image (e.g., a coronal cross-sectional image, a sagittal cross-sectional image, an MPR image, a volume rendering image, an MIP image, or the like). The distance from the vertex position may be specified in an initial setting as "2 centimeters from the vertex position toward the head side" or may be manually set by the operator when the superimposed image is displayed or the like, as, for example, "1.5 centimeters from the vertex position toward the head side". Further, it is acceptable for the controlling unit 36 to cause various types of images to be displayed by using both the vertex position and a position that is a predetermined distance away from the vertex position.

Next, a process performed by the image processing apparatus 30 according to the present embodiment will be explained, with reference to FIG. 8. FIG. 8 is a flowchart for explaining the process performed by the image processing apparatus according to the present embodiment.

As shown in FIG. 8, the image processing apparatus 30 according to the present embodiment judges whether a designation of a three-dimensional medical image to be used as an image processing target is received (step S101). In this situation, if no designation of a three-dimensional medical image to be used as the image processing target is received (step S101: No), the image processing apparatus 30 goes into a stand-by state.

On the contrary, if a designation of a three-dimensional medical image to be used as the image processing target is received (step S101: Yes), the image processing apparatus 30 reads the designated three-dimensional medical image (step S102). For example, the image processing apparatus 30 reads a three-dimensional X-ray CT image capturing a chest of a subject.

Further, the lung field region extracting unit 33 extracts a lung field region from the three-dimensional medical image, based on the pixel values of the pixels constituting the three-dimensional medical image (step S103; see FIG. 3).

After that, the lung field bottom region extracting unit 34 extracts a lung field bottom region from the lung field region extracted by the lung field region extracting unit 33 (step S104; see FIG. 4). The detecting unit 35 detects a vertex position on the head side of the subject, from the lung field bottom region extracted by the lung field bottom region extracting unit 34 (step S105; see FIGS. 5 and 6A to 6D).

Further, the controlling unit 36 exercises control so that the detection result of the detecting unit 35 is displayed on the display unit 32 (step S106), and the process is thus ended. In other words, the controlling unit 36 exercises control so that at least one of the following is displayed on the display unit 32: an axial cross-sectional image obtained by sectioning the three-dimensional medical image at the axial plane that goes through the vertex position detected by the detecting unit 35; and a superimposed image obtained by superimposing the position of such an axial cross-sectional image onto another image of the three-dimensional medical image. Alternatively, the controlling unit 36 exercises control so that at least one of the following is displayed on the display unit 32: an axial cross-sectional image obtained by sectioning the three-dimensional medical image at an axial plane positioned at a predetermined distance from the vertex position; and a superimposed image obtained by superimposing the position of such an axial cross-sectional image onto another image of the three-dimensional medical image.

As explained above, according to the present embodiment, the lung field region extracting unit 33 extracts the lung field region from the three-dimensional medical image, based on the pixel values of the pixels constituting the three-dimensional medical image capturing the chest of the subject. The lung field bottom region extracting unit 34 extracts the lung field bottom region from the lung field region extracted by the lung field region extracting unit 33. The detecting unit 35 detects the vertex position on the head side of the subject from the lung field region bottom region extracted by the lung field bottom region extracting unit 34. The controlling unit 36 exercises control so that at least one of the following is displayed on the display unit 32: the axial cross-sectional image obtained by sectioning the three-dimensional medical image at the axial plane that goes through the vertex position detected by the detecting unit 35; an axial cross-sectional image obtained by sectioning the three-dimensional medical image at an axial plane positioned at a predetermined distance from the vertex position; and the superimposed image obtained by superimposing the position of such an axial cross-sectional image onto another image of the three-dimensional medical image.

In other words, according to the present embodiment, it is possible to automatically determine the position of the top portion of the diaphragm by using an objective judgment criterion, which is the vertex position of the lung field bottom region. Consequently, according to the present embodiment, it is possible to simply and quickly determine the position of the top end of the diaphragm with reproducibility. Further, according to the present embodiment, in compliant with the guideline for making an image diagnosis of emphysema, it is possible to display "the axial cross-sectional image at the top portion of the diaphragm or the axial cross-sectional image at the position that is the predetermined distance away from the top portion of the diaphragm" and to display "the image obtained by superimposing the position of the top portion of the diaphragm or the position that is the predetermined distance away from the top portion of the diaphragm, onto any of the various types of images of the three-dimensional medical image". As a result, according to the present embodiment, it is possible to efficiently aid the image diagnosis process related to emphysema.

Further, according to the present embodiment, the lung field region extracting unit 33 extracts the air region by identifying the pixels of each of which the pixel value is equal to or smaller than the predetermined threshold value, from among the pixels constituting the three-dimensional medical image. Also, the lung field region extracting unit 33 extracts the lung field region by implementing the region growing method while using one of the pixels within the extracted air region as the seed point. Further, the lung field bottom region extracting unit 34 judges whether each of the pixels in the three-dimensional medical image is one of the pixels extracted as those in the lung field region by using the plurality of scanning directions along the body axis direction extending from the legs toward the head of the subject and further extracts the region formed by the pixels each of which is the first pixel judged to be in the lung field region in a different one of the scanning directions, as the lung field bottom region. In other words, according to the present embodiment, it is possible to perform the lung field region extracting process and the lung field bottom region extracting process in a simple manner, based on the characteristics of the medical image used as the image processing target.

Further, according to the present embodiment, the detecting unit 35 detects the vertex position, based on the area size of the lung field bottom region on each of the plurality of axial planes of the three-dimensional medical image within the range in which the lung field bottom region is present. During this process, a situation is anticipated in which the region extracted as the lung field region may include regions that are not in the lung field (e.g., air regions of the trachea and the bronchi). In that situation, the lung field bottom region mask includes some parts that are not in the lung field bottom region. As a result, even if the vertex of the lung field bottom region mask is simply determined, the determined vertex position may not indicate the position of the top portion of the diaphragm.

To cope with this situation, in the present embodiment, to avoid the situation where a part that is not in the lung field bottom region is detected as the position of the top portion of the diaphragm, the quantity of the pixels forming the lung field bottom region is counted for each of the plurality of axial planes in the lung field bottom region mask, so that the position of the axial plane in the highest position among the axial planes judged to have larger counts (larger area sizes) is detected as the vertex position (i.e., the position of the top portion of the diaphragm). In other words, according to the present embodiment, it is possible to detect the vertex position by identifying the range of the lung field bottom region mask judged to be truly in contact with the diaphragm for the reason that the surrounding thereof is occupied by the lung field bottom region. Consequently, according to the present embodiment, it is possible to improve the level of precision in detecting the position of top portion of the diaphragm.

Further, according to the present embodiment, the lung field region extracting unit 33 extracts the right lung field region by implementing the region growing method while using one of the pixels in the region positioned on the right-hand side of the subject within the air region, as the seed point. Further, the lung field bottom region extracting unit 34 extracts the lung field bottom region from the right lung field region extracted by the lung field region extracting unit 33.

In other words, according to the present embodiment, only the right lung field region is used as the processing target based on the anatomic knowledge that the position of the top end of the diaphragm in the right lung field has a high possibility of being the position of the top end of the entire diaphragm. As a result, according to the present embodiment, it is possible to reduce the load in the image processing process and to perform the process to determine the position of the top end of the diaphragm more quickly.

The exemplary embodiments above are explained by using the example in which the lung field bottom region is extracted only from the right lung field region so as to detect the vertex position of the lung field bottom region. However, in the exemplary embodiments, it is acceptable to perform the process to extract the lung field bottom region and the process to detect the vertex position, also with respect to the left lung field region. In that situation, the detecting unit 35 compares the vertex positions of the lung field bottom regions on the left and the right with each other and detects the higher vertex position as the top end of the diaphragm.

It is also acceptable to implement the image processing method described in the exemplary embodiments above in a medical image diagnosis apparatus that took the three-dimensional medical image used as the image processing target. In other words, in the exemplary embodiments described above, it is acceptable to incorporate the image processing apparatus 30 into an X-ray CT apparatus, an X-ray diagnosis apparatus, an MRI apparatus, or the like.

As explained above, according to the exemplary embodiments, it is possible to simply and quickly determine the position of the top end of the diaphragm with reproducibility.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
processing circuitry configured to
extract, based on pixel values of pixels in a three-dimensional medical image capturing a chest of a subject, a lung field region from the three-dimensional medical image;
judge, in a plurality of scanning directions along a body axis direction that extends from legs of the subject toward a head of the subject, whether each of the pixels in the three-dimensional medical image is one of pixels in a lung field region;
extract, as the lung field bottom region, a region formed by pixels in which each is a first pixel judged, in a different scanning direction of the plurality of scanning directions, to be in the lung field region; and
detect a top end position of a diaphragm by detecting a vertex position of the lung field bottom region on a head side of the subject, the top end position of the diaphragm being a part of the diaphragm that is closest to the head of the subject, wherein
the processing circuitry detects the vertex position based on an area size of the lung field bottom region on each of a plurality of axial planes of the three-dimensional medical image within a range in which the lung field bottom region is present.

2. The image processing apparatus according to claim 1, wherein the processing circuitry is further configured to exercise control so that at least one of following is displayed on a predetermined display:
an axial cross-sectional image obtained by sectioning the three-dimensional medical image at an axial plane going through the vertex position;
an axial cross-sectional image obtained by sectioning the three-dimensional medical image at an axial plane positioned at a predetermined distance from the vertex position; and
a superimposed image obtained by superimposing a position of the axial cross-sectional image onto another image of the three-dimensional medical image.

3. The image processing apparatus according to claim 1, wherein the processing circuitry extracts the lung field region by identifying pixels that are of a pixel value that is equal to or smaller than a predetermined threshold value from among the pixels constituting the three-dimensional medical image so as to extract an air region and implementing a region growing method while using one of the pixels within the extracted air region as a seed point.

4. The image processing apparatus according to claim 3, wherein the processing circuitry is further configured to
extract a right lung field region by implementing a region growing method while using one of pixels in a region positioned on a right-hand side of the subject within the air region as a seed point, and
extract the lung field bottom region from the right lung field region.

5. An image processing method, comprising:
extracting, by processing circuitry based on pixel values of pixels in a three-dimensional medical image capturing a chest of a subject, a lung field region from the three-dimensional medical image;
judging, by the processing circuitry, in a plurality of scanning directions along a body axis direction that extends from legs of the subject toward a head of the subject, whether each of the pixels in the three-dimensional medical image is one of pixels in a lung field region;
extracting, by the processing circuitry, as the lung field bottom region, a region formed by pixels in which each is a first pixel judged, in a different scanning direction of the plurality of scanning directions, to be in the lung field region; and
detecting, by the processing circuitry, a top end position of a diaphragm by detecting a vertex position of the lung field bottom region on a head side of the subject, the top end position of the diaphragm being a part of the diaphragm that is closest to the head of the subject, wherein
the processing circuitry detects the vertex position based on an area size of the lung field bottom region on each of a plurality of axial planes of the three-dimensional medical image within a range in which the lung field bottom region is present.

* * * * *